(12) United States Patent
Kirn

(10) Patent No.: US 8,972,018 B2
(45) Date of Patent: Mar. 3, 2015

(54) ADAPTIVE MUSCLE STIMULATION TECHNIQUE

(71) Applicant: Larry Joseph Kirn, Austin, TX (US)

(72) Inventor: Larry Joseph Kirn, Austin, TX (US)

(73) Assignee: Articulate Labs, Inc., Austin, TX (US)

( * ) Notice: Subject to any disclaimer, the term of this patent is extended or adjusted under 35 U.S.C. 154(b) by 0 days.

(21) Appl. No.: 13/847,915

(22) Filed: Mar. 20, 2013

(65) Prior Publication Data

US 2013/0253607 A1     Sep. 26, 2013

Related U.S. Application Data

(60) Provisional application No. 61/613,288, filed on Mar. 20, 2012, provisional application No. 61/649,452, filed on May 21, 2012.

(51) Int. Cl.
| | | |
|---|---|---|
| *A61N 1/36* | (2006.01) | |
| *A61B 5/11* | (2006.01) | |
| *A61B 5/04* | (2006.01) | |
| *A61B 5/00* | (2006.01) | |

(52) U.S. Cl.
CPC ............ *A61N 1/36003* (2013.01); *A61B 5/112* (2013.01); *A61N 1/36014* (2013.01); *A61B 5/04* (2013.01); *A61B 5/4585* (2013.01); *A61B 5/4836* (2013.01); *A61B 2562/0219* (2013.01)
USPC .............................................. 607/48; 607/49

(58) Field of Classification Search
CPC ................................................. A61N 1/36003
See application file for complete search history.

(56) References Cited

U.S. PATENT DOCUMENTS

| | | | | |
|---|---|---|---|---|
| 5,628,722 | A | * | 5/1997 | Solomonow et al. ........... 602/26 |
| 7,822,481 | B2 | | 10/2010 | Gerber et al. |
| 8,060,210 | B1 | | 11/2011 | Carroll et al. |
| 2007/0208392 | A1 | * | 9/2007 | Kuschner et al. ............... 607/48 |
| 2011/0015696 | A1 | | 1/2011 | Kirn |
| 2011/0034797 | A1 | | 2/2011 | Savard et al. |

FOREIGN PATENT DOCUMENTS

WO     2012-047737      4/2012

OTHER PUBLICATIONS

Patent Cooperation Treaty, Korean Intellectual Property Office, Notification of Transmittal of the International Search Report and the Written Opinion of the International Searching Authority, mailed Jul. 11, 2013, in international application No. PCT/US2013/033190.

* cited by examiner

*Primary Examiner* — Michael Kahelin
(74) *Attorney, Agent, or Firm* — Trop, Pruner & Hu, P.C.

(57) ABSTRACT

An embodiment of the invention resides in the apparatus and technique of dynamically measuring and storing a biological condition or disposition during the time that one set of conditions are imposed on a joint or body area and applying closed-loop therapeutic action so as to re-achieve that same biological condition or disposition during a subsequent time that another different set of conditions are imposed. Furthermore, dynamic potentials surrounding said joint or body area may be created, bolstered, and/or modulated through aspects of stimulation applied which are independent of those aspects utilized to counteract force incident on the joint or body area. Other embodiments are described herein.

16 Claims, 10 Drawing Sheets

ADAPTIVE MUSCLE STIMULATION TECHNIQUE

This application claims priority to both (a) U.S. Provisional Patent Application No. 61/613,288 filed on Mar. 20, 2012 and entitled "Adaptive Muscle Stimulation Technique", and (b) U.S. Provisional Patent Application No. 61/649,452 filed on May 21, 2012 and entitled "Adaptive Tissue Stimulation Technique". The content of both provisional applications is hereby incorporated by reference.

BACKGROUND

When a skeletal joint is compromised, whether through injury, pathology, misalignment, overuse, or surgery, bracing is often necessary to provide support and possibly facilitate healing. Conventional external mechanical braces, however, have been shown repeatedly to cause muscle atrophy by supplanting normal muscle activity. In that this effect is antipathetic to the basic principles of rehabilitation, devices which actively stimulate the body's own musculature surrounding the compromised joint are increasingly being used for protection and/or rehabilitation. One of these devices may be worn throughout the day, constantly monitors the patient's movements, and responds to problematic joint circumstances by stimulating muscles in a manner which opposes the incident force causing the problem. A form of muscle stimulation used in these devices is electrical current.

These devices, however, rely upon pre-programmed templates for operational parameters, or learn physical conditions deemed problematic for the joint by either the patient or an attending medical practitioner. They are therefore inherently open-loop systems, responsive solely to physical conditions of the joint, without regard for direct or indirect effects of the dynamic muscle stimulation they provide. Not only does this open-loop nature necessitate programming applicable to a broad range of patients (as opposed to individualized therapy), it as well precludes adaptation by the device to incremental improvements made by the patient through use of the device. No attempt may therefore be made by such a system to regulate therapy toward a nominal state for that particular patient. Application of closed-loop techniques would allow these devices to continuously adapt to the individual patient on an ongoing basis.

The term 'closed-loop' is used herein to denote proportional control of a control system output (such as electrical muscle stimulation current), as a linear or non-linear function of one or more error terms. These error terms, as commonly practiced in the art, consist of deviations between a desired value of a measured input (command term) and the actual measured input.

Bones and joints both have been known for some time to exhibit piezoelectric properties. Following the discoveries that bones become stronger in adaptation to stress, and that physical stress induces localized currents in the bone, bone growth stimulators have been developed which apply controlled mechanical stress and/or electrical current to a damaged tissue area. Consistent with observed piezoelectric activity and stress-induced growth of bone and joints, electrical stimulation which imposes a DC bias has shown to accelerate tissue regeneration.

Piezoelectric activity is considered to be a minor contributor to natural electrical currents in and near joints. Each change in skeletal loading causes fluid flow through bone and particularly cartilage. Due to constituent charged particles, this fluid flow creates dynamic electrical currents which impose what are referred to as streaming potentials across the surrounding tissue. Streaming potentials have significance both from a diagnostic perspective, and in their capacity for fluid flow modulation. In addition to possible impact on cartilage hydration in eroded joints through imposed steaming potentials, control of chondrocyte migration has been shown to occur from imposed electrical potentials.

Diagnostic measurement of joint potentials under dynamic loading is taught in U.S. Patent Application Publication No. 20110034797, 'Non-invasive measuring of load-induced electric potentials in diarthroidal joints'. Neither use of the subject matter of the application outside a diagnostic setting, nor therapeutic modulation of potentials discovered is addressed. Furthermore, the subject matter of the application does not address the relationships between the myriad force vectors possible during normal activity and the resultant streaming potentials. Vectors of incident forces upon a joint become much more significant when applied to joints comprised of multiple load-bearing surfaces.

To date, devices that stimulate bone and cartilage growth through electrical stimulation have relied either upon constant excitation or pre-programmed stimulation sequences. In contrast, piezoelectric activity and streaming potentials during normal patient activities are dynamic—polarities and magnitudes of the currents generated are resultant of incident forces, so constantly follow physical activity. Stimulation devices which are non-responsive to physical activity therefore are incapable of either mimicking or bolstering natural biological piezoelectric or streaming potential activity. In that it has been found that synchronizing muscle stimulation with volitional exertion, it is improved tissue regeneration may result from synchrony between physical stress and stimulation. To compound difficulty in bolstering or supplanting this electrical activity of a specific patient, huge subject response variances have been reported. This strongly implies that broad success of generalized stimulation will be less probable without adaptation to each specific case.

Synchronization of stimulation to the gait cycle, for the purpose of impacting cartilage health, is explored in U.S. Pat. No. 8,060,210, 'Methods for improving mobility and controlling cartilage matrix degradation of weight-bearing articular joints'. The subject matter of this patent addresses motor-level stimulation of antagonistic muscles in a timed fashion, so as to minimize pressure or moving friction, but makes no distinction between reduced joint forces through muscle contraction and charged particle migration through the joint tissue. In that timing, physical location, and stimulation waveforms required for joint force reduction may or may not differ substantially from those required for fluid flow modulation, the arbitrary application of waveforms before and/or after application of unspecified multiphasic stimulation, as taught therein, does not show independent fluid flow control.

U.S. Pat. No. 7,822,481 addresses adjustment of a therapy program in response to one or more sensed patient parameters, but does not describe stimulation intensity to be any direct function of patient activity or circumstance. Adaptation by stimulators to dynamic physical conditions can be found both in cardiac stimulators and neural stimulators used for pain masking, such as is disclosed in U.S. Pat. No. 7,822,481, 'Therapy adjustment'. These devices alter one or more parameters of pre-programmed stimulation patterns in response to body position or inclination, activity level, etc. None of these devices, however, stimulate tissue as a direct function of dynamic physical conditions imposed on the stimulated area.

BRIEF DESCRIPTION OF THE DRAWINGS

Embodiments of the present invention will be described by way of exemplary embodiments, but not limitations, illustrated in the accompanying drawings in which like references denote similar elements, and in which.

DETAILED DESCRIPTION

Figure 1:
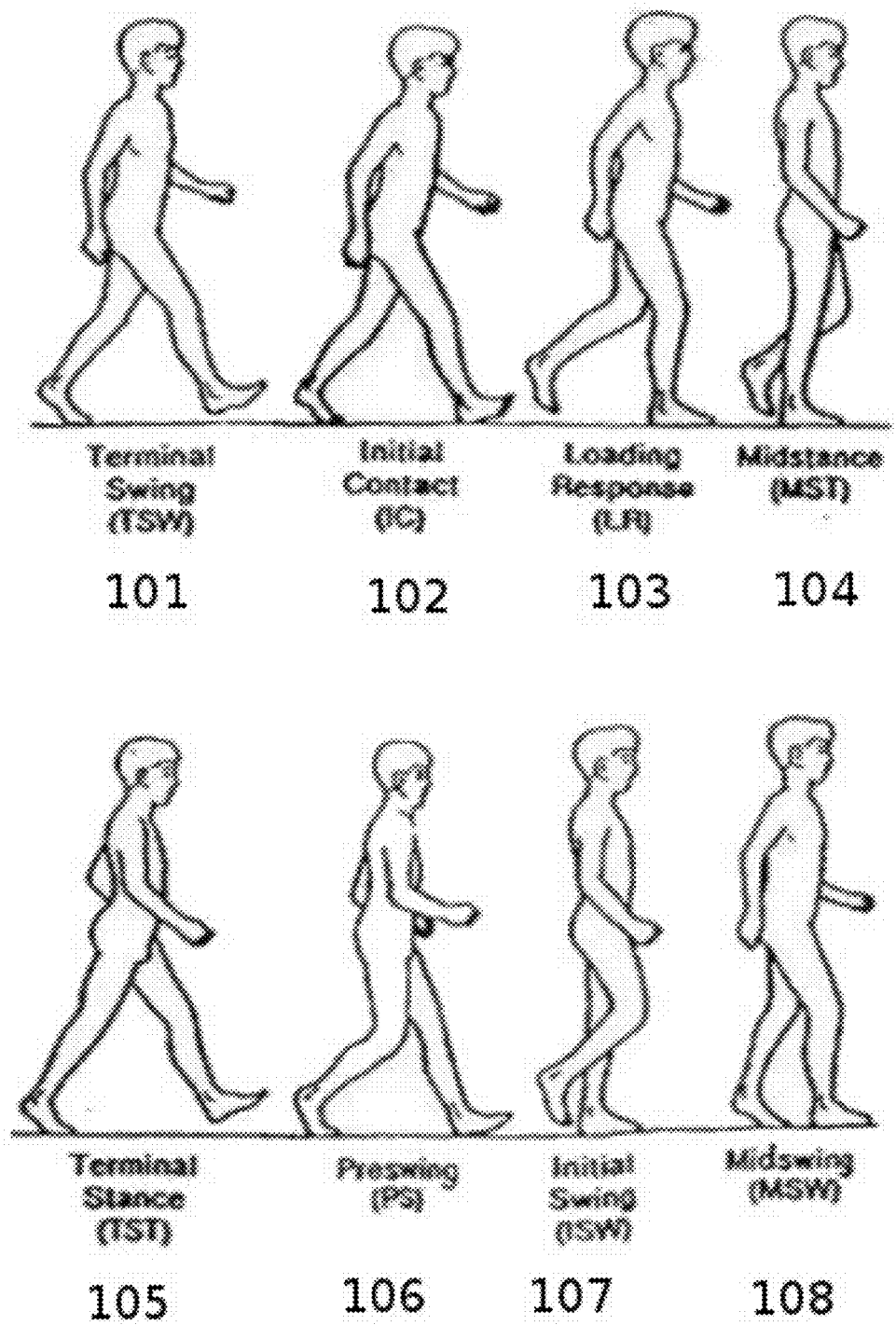
FIG. 1 shows commonly-recognized segments, known as phases, of the right-leg gait cycle of a person while walking.

Various operations will be described as multiple discrete operations, in turn, in a manner that is most helpful in understanding the illustrative embodiments; however, the order of description should not be construed as to imply that these operations are necessarily order dependent. In particular, these operations need not be performed in the order of presentation. Further, descriptions of operations as separate operations should not be construed as requiring that the operations be necessarily performed independently and/or by separate entities. Descriptions of entities and/or modules as separate modules should likewise not be construed as requiring that the modules be separate and/or perform separate operations. In various embodiments, illustrated and/or described operations, entities, data, and/or modules may be merged, broken into further sub-parts, and/or omitted. The phrase "embodiment" is used repeatedly. The phrase generally does not refer to the same embodiment; however, it may. The terms "comprising," "having," and "including" are synonymous, unless the context dictates otherwise. The phrase "A/B" means "A or B". The phrase "A and/or B" means "(A), (B), or (A and B)". The phrase "at least one of A, B and C" means "(A), (B), (C), (A and B), (A and C), (B and C) or (A, B and C)".

Although diagnostic measurement of joint potentials under dynamic loading in a clinical setting is addressed in U.S. Patent Application Pub. No. 20110034797, 'Non-invasive measuring of load-induced electric potentials in diarthroidal joints', modulation of the streaming potentials involved as a continuous patient resource (outside clinical settings) is included in an embodiment of the invention and facilitates tissue preservation and/or possibly regeneration when combined with protective measures, such as those afforded by surrounding musculature.

In addition to dynamic electrical activity within tissue with readily observable relationships to physical activity, longer-term dynamic electrical potentials have repeatedly been observed. In that this activity has often been associated with pathological states or recovery therefrom, modulation of dynamic potentials at very low frequencies is included in an embodiment of the invention.

In that ambulant muscle stimulators are most often applied to areas which have been physically damaged, extension past their current use for physical support, to encourage tissue hydration and regeneration, is addressed in an embodiment of the invention.

An embodiment satisfies a need whereby ambulant muscle stimulation may be modulated to both counteract forces incident on an area of a body in a closed-loop fashion, and to encourage tissue generation or regeneration by stimulating localized tissue in a manner highly consistent with individualized biological activity.

An embodiment of the invention resides in the apparatus and technique of dynamically measuring and storing a biological condition or disposition during the time that one set of conditions are imposed on a joint or body area and applying closed-loop therapeutic action so as to re-achieve that same biological condition or disposition during a subsequent time that another different set of conditions are imposed. Furthermore, dynamic potentials surrounding said joint or body area may be created, bolstered, and/or modulated through aspects of stimulation applied which are independent of those aspects utilized to counteract force incident on the joint or body area.

Referring now to FIG. 1, Terminal Swing 101 shows the end of travel forward of the right foot, in preparation for taking a step. Initial Contact 102 shows the right foot being planted, or loaded. Note that the left foot is as well load-bearing at this time. Loading Response 103 shows full loading of the right foot as the left foot leaves the ground. Midstance 104 shows the point of maximal gravitic load on the right foot. Terminal Stance 105 shows forward propulsion changing from the upper-leg muscles to the muscles of the lower leg. Preswing 106 shows the end of propulsion by the lower leg muscles, hence the end of ankle travel (plantarflexion), in preparation to swing the right leg forward for another step. Initial Swing 107 shows the right foot lifting from the ground and initial femur travel forward. Midswing 108 shows the end of femur travel with continuation of tibia travel forward.

From the previous delineations, it can be seen that the right leg supports body weight through Phases 102, 103, 104, 105, and 106; but is in free space through Phases 107, 108, and 101. It can also be seen that the femur and tibia are in higher axial alignment in Phase 101 than Phases 107 or 108.

Figure 2:
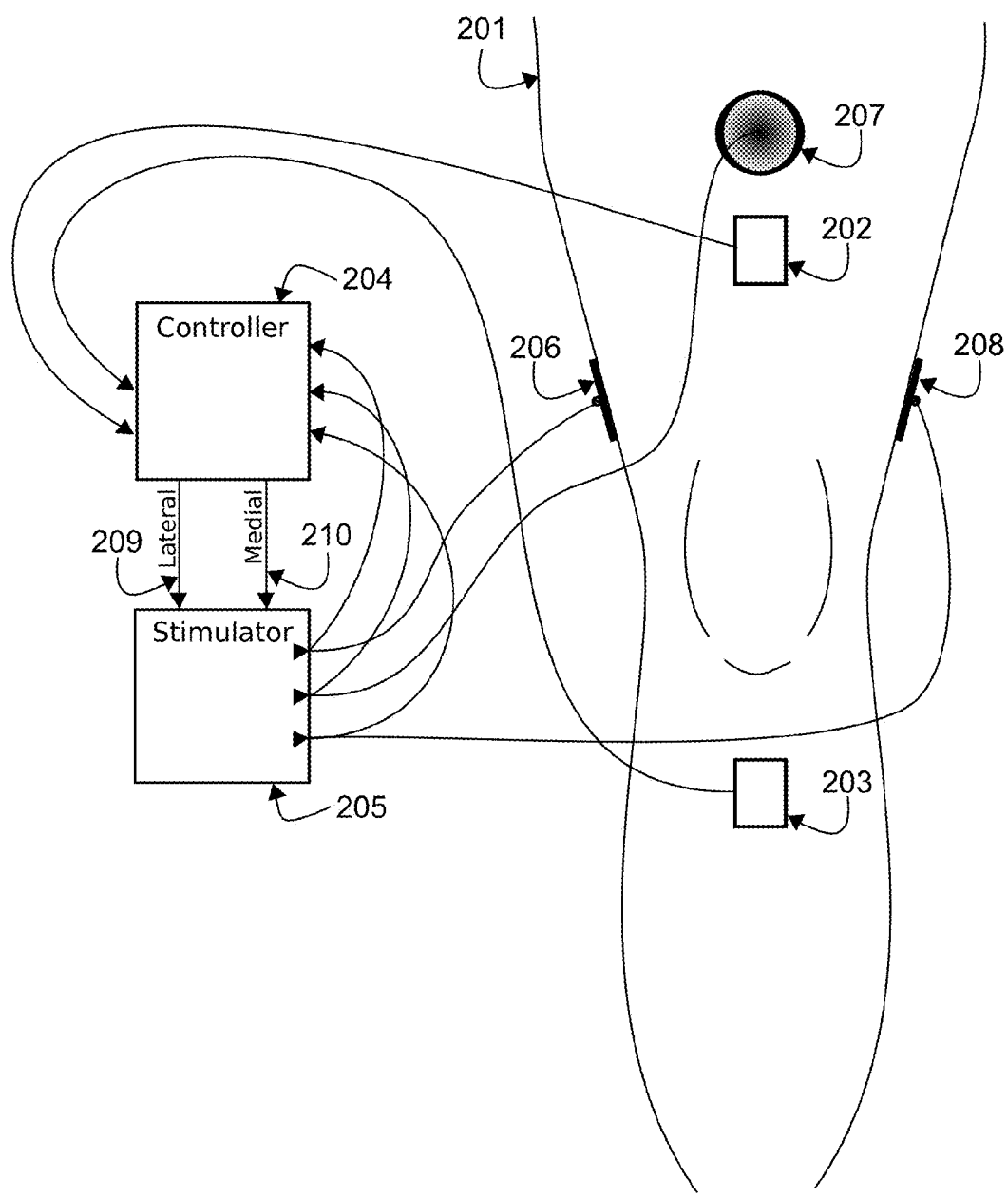
FIG. 2 shows an anterior view of an apparatus for an embodiment of the invention, as applied to a right human knee.

Referring now to FIG. 2, three-axis Accelerometers 202 and 203 are mounted on the anterior surface of Leg 201. Stimulation Electrodes 206, 207, and 208 are as well affixed to Leg 201 at lateral, central, and medial locations over quadriceps muscles, respectively. Stimulation Amplifier 205 outputs differential constant-current stimulation pulses to Electrodes 206 and 207 to contract lateral musculature, and/or Electrodes 208 and 207 to contract medial musculature.

Controller 204 receives positional information in the sagittal and coronal planes of the femur from Accelerometer 202, and of the tibia from Accelerometer 203, respectively. Accelerometers 202 and 203 sense positions and motions in three axes. Controller 204 as well receives input from Electrodes 206, 207, and 208. These inputs are used by Controller 204 to produce Medial Stimulation 209 and Lateral Stimulation 210, both of which are applied as control inputs to Stimulation Amplifier 205.

Figure 3:
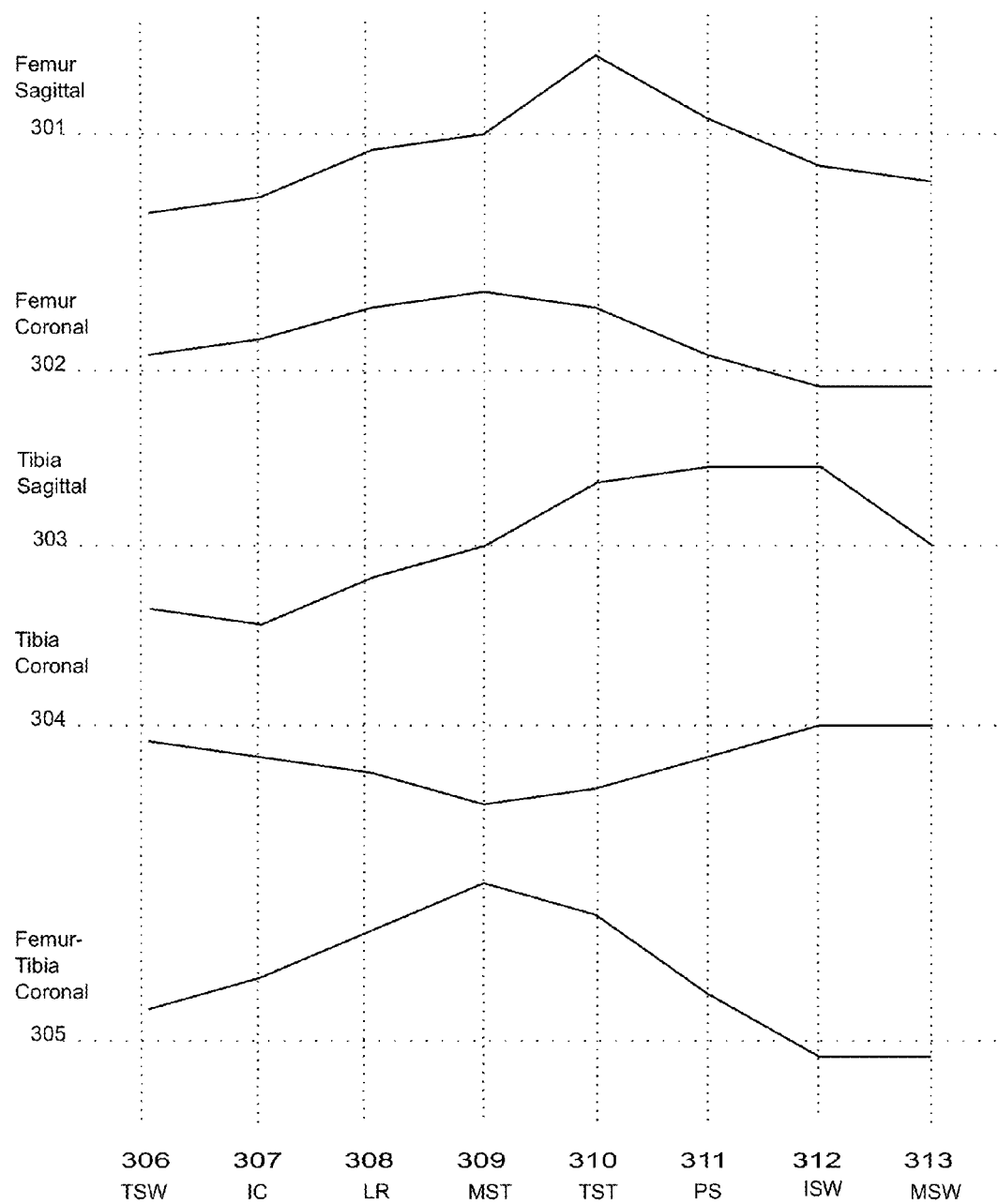
FIG. 3 shows positional information in the sagittal and coronal planes of a person proceeding through the gait cycle of FIG. 1.

Referring now to FIG. 3, Position 301 shows sagittal position of the right femur, Position 302 shows coronal position of the right femur, Position 303 shows sagittal position of the right tibia, Position 304 shows coronal position of the right tibia, and Position Differential 305 shows right leg differential femur-tibia coronal position, all of the person proceeding through the gait phases of FIG. 1. Phase markers 306, 307, 308, 309, 310, 311, 312, and 313 show positions at gait Phases 101, 102, 103, 104, 105, 106, 107, and 108, respectively, all of FIG. 1. Sagittal positions increase with motion in a posterior direction; coronal positions increase with motion in a lateral direction (abduction). Central axis marked for each Position indicates true vertical. (Horizontal dotted lines are plumb verticals in both sagittal and coronal planes.)

Although inertial forces will often exceed gravitic forces during normal activities, gravitic forces only are included herein in the interest of simplicity. It is assumed that the person depicted in FIG. 1 and measured in FIGS. 3 and 5 suffers medial condyle damage which results in collapse on that condyle when the knee is under compressive load. This collapse results in a lateral deflection of the knee, known as a varus deformity.

At Marker 309, corresponding to Midstance 104, of FIG. 1, note that femur sagittal Position 301 and Tibia sagittal Position 303 are both mid-scale, indicating true vertical for both femur and tibia. Maximum gravitic axial force occurs at this inclination. Note as well that femur coronal Position 302 indicates largest lateral deflection and that tibia coronal Position 304 indicates medial deflection at Marker 309, consistent with medial condyle collapse. The differential coronal Position 305 therefore indicates degree of varus deformity, maximum deformity being at Marker 309 as the leg withstands maximum gravitic axial force.

Note that at Markers 312 and 313, corresponding to Initial Swing 107 and Midswing 108 of FIG. 1, the femur swings slightly in the medial direction, shown in femur coronal Position 302. This medial motion represents compensatory reaction taken against the previous lateral collapse.

Note however, that at Marker 306, corresponding to Terminal Swing 101 of FIG. 1, that femur and tibia coronal positions 302 and 304 achieve balance. This is presumably in response to full quadriceps firing, extending the tibia in preparation for landing the next step. With similar muscle activation, therefore, the primary physical difference between Markers 306 and 307, corresponding to Terminal Swing 101 and Initial Contact 102, of FIG. 1, is compressive loading on the leg.

Lateral laxity in the proposed example results in the progressive varus deformity seen between Markers 307 and 311 in differential femur-tibia coronal Position 305. A perfect hinge joint, however, would maintain a constant value in Position 305, and a healthy knee may be expected to maintain a relatively constant value between at least Positions 306 and 311, corresponding to Terminal Swing 101 and Preswing 106 of FIG. 1. In other words, compressive force should create no (or little) significant coronal deviation from the differential Position 305 seen at Marker 306. In that the differential coronal position is not impacted by loading, Terminal Swing 101 of FIG. 1 therefore represents an optimal target for differential position of the knee, regardless of laxity within the joint.

Figure 4:
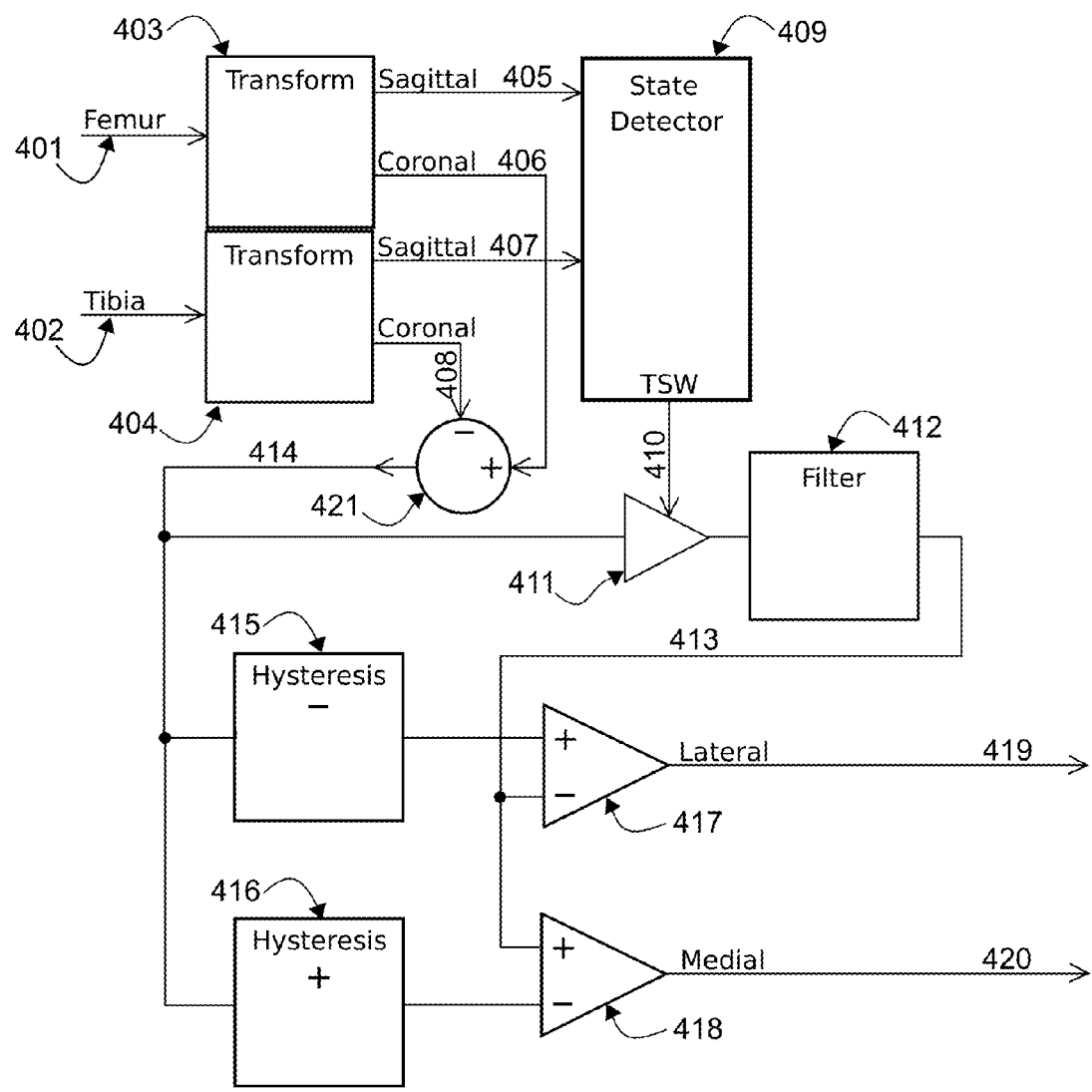
FIG. 4 shows functional elements of an embodiment of the invention operative to counteract incident forces, such as to be included within Controller 204 of FIG. 2.

Referring now to FIG. 4, Accelerometer Output 401, from Accelerometer 202 of FIG. 2, and Accelerometer Output 402, from Accelerometer 203 of FIG. 2, are applied as inputs to Spacial Transforms 403 and 404, respectively. Transforms 403 and 404 derive sagittal and coronal positions from said three-axis accelerometers, using techniques known to the art. Femur Sagittal Position 405 and tibia Sagittal Position 407 are applied as inputs to State Detector 409, which continuously detects if Leg 201 of FIG. 2 is in the Terminal Swing Phase 101 or state, of FIG. 1, and outputs this result as TSW State Indication 410.

Femur Coronal Position 406 and tibia Coronal Position 408, output by Transforms 403 and 404, respectively, are applied as non-inverting and inverting inputs, respectively, of Summer 421. Summer 421 provides as output Femur-Tibia Coronal Differential 414, which is shown in Trace 305 of FIG. 3. Femur-Tibia Coronal Differential 414 is applied as signal input to Amplifier 411, and TSW State Indication 410 is applied as enable input to Amplifier 411, which gates Femur-Tibia Coronal Differential 414 to Filter 412 only during the times that State Detector 409 detects that the system of FIG. 2 is in Terminal Swing Phase 101 of FIG. 1. The Target Coronal Differential 413 of Filter 412 therefore consists of the average Femur-Tibia Coronal Differential of Leg 201 of FIG. 2 during Terminal Swing Phase 101 of FIG. 1.

Target Coronal Differential 413 is applied as input to Hysteresis Adder 415, which adds a negative value, and Hysteresis Adder 416, which adds a positive value.

The output of Hysteresis Adder 415 and Target Coronal Differential 413 are supplied as non-inverting and inverting inputs, respectively, to Amplifier 417. The output of Amplifier 417 therefore is a value which increases as Femur-Tibia Coronal Differential exceeds Target Coronal Differential by the hysteresis amount of Hysteresis Adder 415. The output of Amplifier 417 is output as Lateral Stimulation 419, or 209 of FIG. 2, and used to control lateral stimulation from Stimulation Amplifier 205, also of FIG. 2.

The output of Hysteresis Adder 416 and Target Coronal Differential 413 are supplied as inverting and non-inverting inputs, respectively, to Amplifier 418. The output of Amplifier 418 therefore is a value which increases as Femur-Tibia Coronal Differential falls below Target Coronal Differential by the hysteresis amount of Hysteresis Adder 416. The output of Amplifier 418 is output as Medial Stimulation 420, or 210 of FIG. 2, and used to control medial stimulation from Stimulation Amplifier 205, also of FIG. 2.

Figure 5:
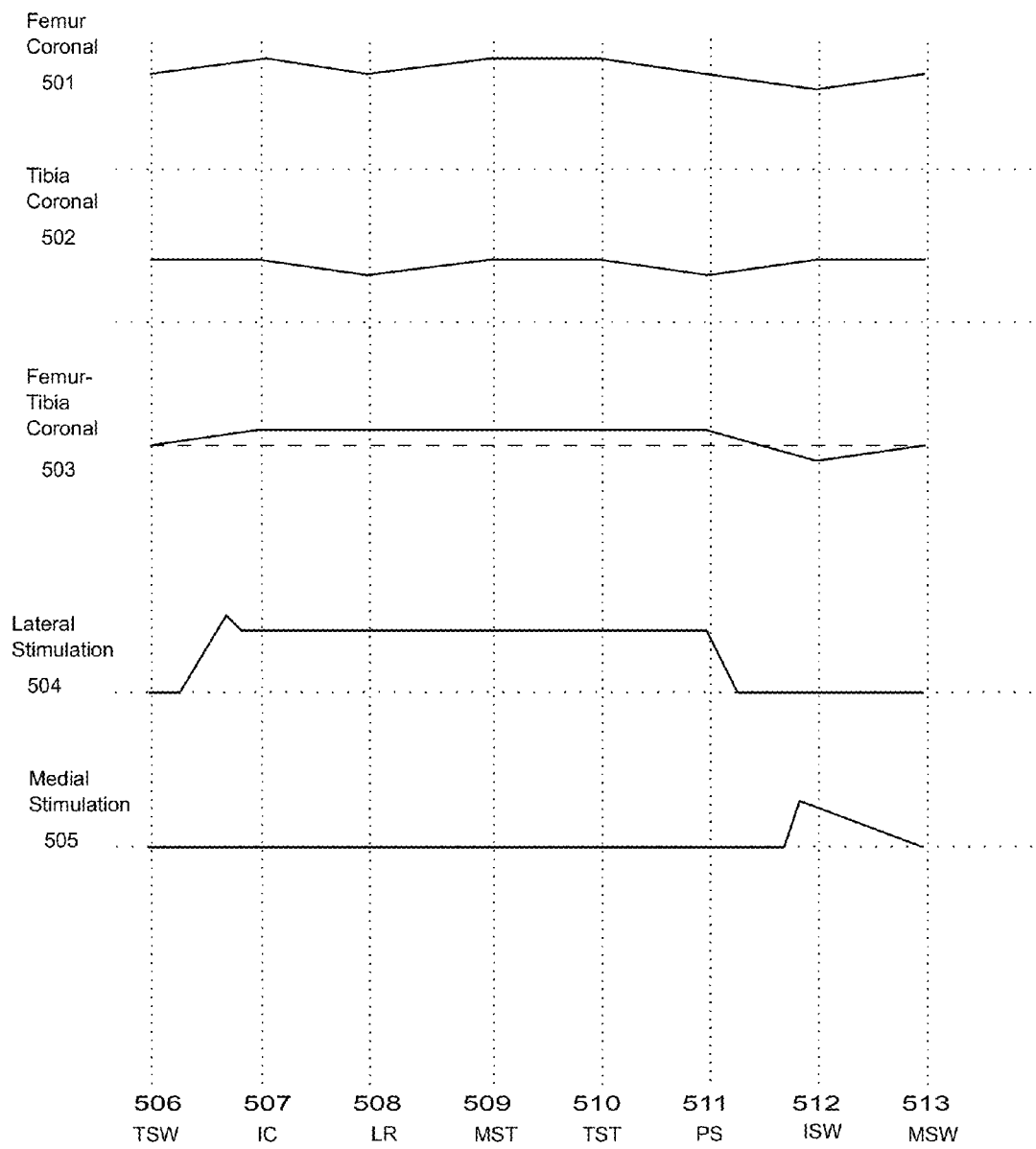
FIG. 5 shows outputs of an embodiment of the invention in response to a user of the embodiment proceeding through the gait cycle of FIG. 1.

Referring now to FIG. 5, Position 501 shows coronal position of the right femur, Position 502 shows coronal position of the right tibia, and Position Differential 503 shows femur-tibia coronal differential of the right leg of the person of FIG. 1. Lateral Stimulation 504 and Medial Stimulation 505 show amplitude of stimulation to be applied to the lateral and medial side of Leg 201 of FIG. 2, respectively. Phase markers 506, 507, 508, 509. 510, 511, 512, and 513 show positions at gait Phases 101, 102, 103, 104, 105, 106, 107, and 108, respectively, all of FIG. 1. Coronal positions increase with motion in a lateral direction (abduction). Central axis marked for each Position indicates true vertical. The heavy dotted line of Position 503 represents the Target Femur-Tibia Coronal Differential 413 of FIG. 4, which can be seen to be the same as the femur-tibia coronal differential shown in Position 503 at Marker 506, corresponding to Terminal Swing 101 of FIG. 1. (Dotted horizontal lines on 501 and 502 are coronal plumb vertical, assuming the leg is abducted from vertical. Heavy dotted horizontal line in 503 is zero Femur/Tibia coronal deviation. Dotted horizontal lines on 504 and 505 are also zero.)

Note that beyond a small error, representing the hysteresis value of Hysteresis Adder 415 of FIG. 4, Lateral Stimulation 504 increases, overshoots, and settles to a constant value as femur-tibia coronal differential exceeds Target 413 of FIG. 4.

After Marker 511, Lateral Stimulation 504 can be seen to return to zero as Differential 503 converges on Target Differential 413 of FIG. 4. Note that Medial Stimulation 505 then increases as Differential 503 falls below Target Differential 413 of FIG. 4 by a small error representing the hysteresis value of Hysteresis Adder 416 of FIG. 4, but falls to zero as Differential 503 again approaches Target Differential 413 of FIG. 4.

Thus, the embodiment of FIG. 2 provides a hysteretic closed-loop system utilizing the lateral and medial muscles of Leg 201 of FIG. 2 as actuators. This is in contrast to conventional systems, wherein open-loop muscle stimulation only is in use. In further contrast to conventional systems, the embodiment can be seen to continuously update an optimal command term for this closed-loop system from biological input of the person using an embodiment of the invention. Resultantly, the embodiment can be seen to not only adapt to the specific user of the embodiment of the invention, but furthermore adapt to ongoing changes in that specific user without external intervention.

Figure 6:
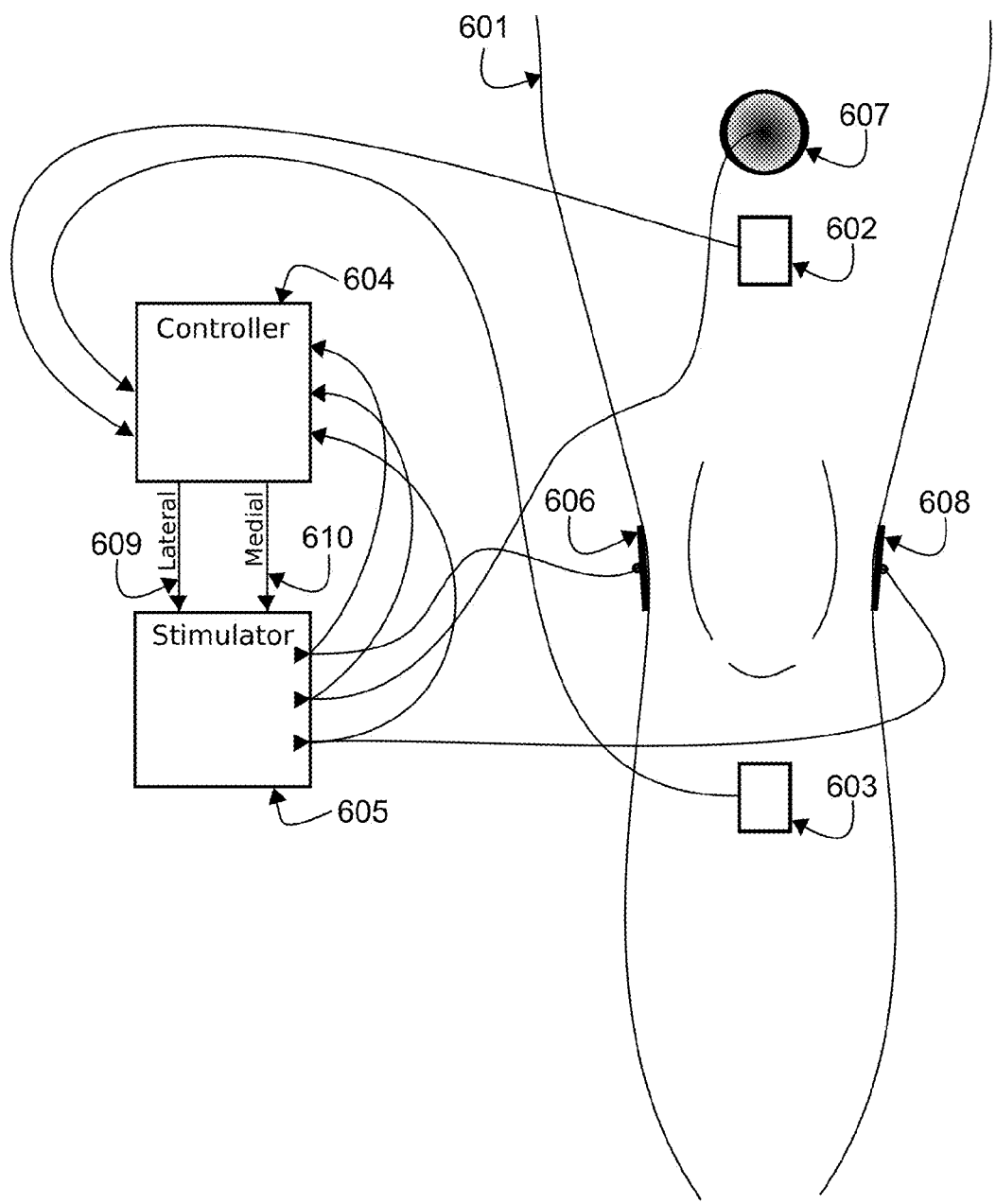
FIG. 6 shows an anterior view of an apparatus for an alternative embodiment of the invention, as applied to a left human knee.

Referring now to FIG. 6, three-axis Accelerometers 602 and 603 are affixed or held in place in the coronal plane over the femur and tibia, respectively, of Leg 601, presumably a human left leg. Electrodes 606 and 608 are affixed or held in place in the sagittal plane at the meniscus, directly over the medial and lateral margins, respectively, of the knee of Leg 601. Electrode 607 is affixed or held in place in the coronal plane, centered on the femur, proximal to the knee. By the orientations shown, it can be seen that electrical potentials created at or around the medial meniscus are differentially presented to Electrodes 606 and 607, and that electrical potentials created at or around the lateral meniscus are differentially presented to Electrodes 608 and 607. Note that FIG. 6 differs from FIG. 2 in placement of Electrodes 606 and 608, which have been moved in a distal direction so as to highlight a specific aspect of an embodiment of the invention.

Controller 604 receives as input accelerations in three axes of the femur from Accelerometer 602 and accelerations in three axes of the tibia from Accelerometer 603. Note that information regarding both gravitic and dynamic accelerations is provided by said Accelerometers.

Both static and dynamic potentials occurring on the surface of Leg 601 are provided to Controller 604 by Electrodes 606, 607, and 608. Direct coupling to Controller 604, to facilitate inspection of both direct and alternating voltage potentials on the surface of Leg 601, is assumed. It is assumed that Controller 604 has adequate processing capability to continuously quantify vectored forces magnitudes, through modeling techniques known to the art, incident upon the knee of Leg 601, using acceleration information in three axes each from Accelerometers 602 and 603. Being in receipt of both Accelerometer 602 and 603 inputs, said processing capability, and Electrode 606, 607, and 608 inputs, it can be seen that Controller 604 has available requisite inputs and capability to ascertain relationships between vectored forces incident upon the knee of Leg 601 and the resultant streaming potentials biologically created within Leg 601. It is also assumed that Controller 604 is possessed of adequate memory to store these relationships so ascertained.

Electrodes 606, 607, and 608 may as well be driven by Muscle Stimulator 605, which may provide stimulation currents to said electrodes under control of Medial and Lateral Stimulation Commands 609 and 610, respectively, issued from Controller 604. Presumably Stimulator 605 will provide differential current between Electrodes 606 and 607 in response to Medial Command 609 from Controller 604, and differential current between Electrodes 608 and 607 in response to Lateral Command 610 from Controller 604. Independent, simultaneous, and time division multiplexing are among the output stimulation capabilities.

Electrodes 606, 607, and 608 therefore serve as both input and indirect output connections to and/or from Controller 604. While Stimulator 605 is providing a current output, voltage measured by Controller 604 will be representative of the impedance presented by Leg 601 to Stimulator 605. While Stimulator is not providing current, the voltage measured by Controller 604 will be representative of residual stimulation charge or potentials biologically created, such as piezoelectric or streaming potentials.

Controller 604 presumably utilizes a constant frequency source, as is commonly practiced, allowing temporal calculations, such as integration, derivation, and/or filtering to be performed upon inputs and/or outputs.

Although differential potentials and currents of medial and lateral condyles only are disclosed herein for the sake of simplicity, other embodiments may include one or more electrodes, using potentials and/or currents across any two or more electrodes or electrode groups.

Note that components shown in FIG. 6 are preferentially situated on or near Leg 601, allowing the wearer to move without encumbrance. This facilitates use outside a clinical setting, during normal daily activities of any user.

It can therefore be seen that Controller 604 is possessed of both vectored forces incident upon the knee of Leg 601 during normal activity of the knee of Leg 601, and resultant streaming potentials biologically generated by Leg 601 during these same activities. It can as well be seen that Controller 604 is capable of independent stimulation between at least any two of Electrodes 606, 607, and 608. This combination of input and output capability therefore facilitates potential to modulate biologically-generated streaming forces around the knee of Leg 601 during normal activities. Bipolar stimulation capability is used in some embodiments, facilitating application of time-variant positive and/or negative gradients between electrodes. Positive current, negative current, or alternating current with or without positive or negative integrated charge is therefore available across any electrode pair.

Figure 7:
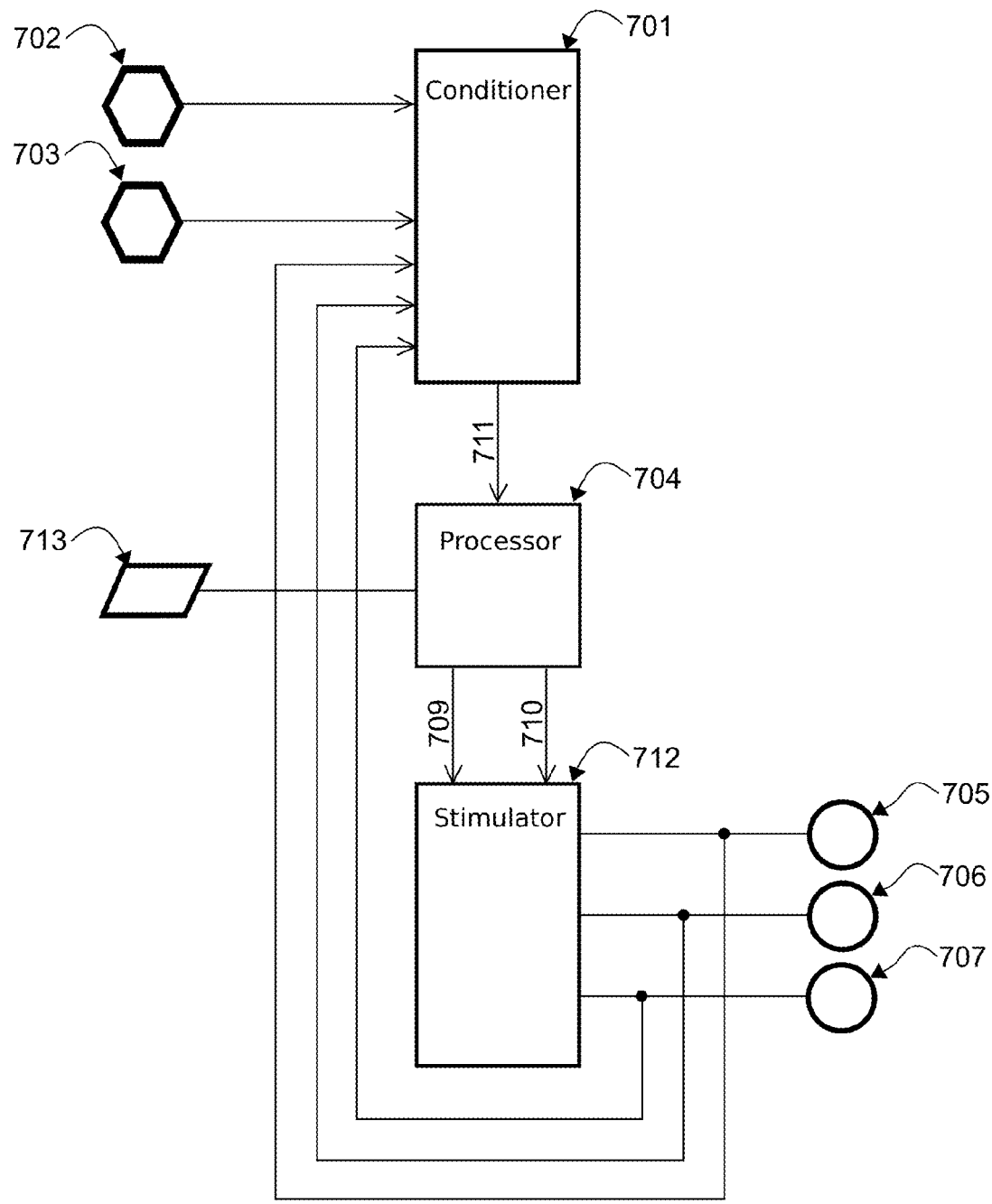
FIG. 7 shows an internal block diagram of an embodiment of the invention operative to create, bolster, and/or modulate dynamic potentials in and around a joint.

Referring now to FIG. 7, three-axis Accelerometers 702 and 703, corresponding to Accelerometers 602 and 603, respectively of FIG. 6, provide sensor input to Signal Conditioner 701. Electrodes 705, 706, and 707, corresponding to Electrodes 605, 606, and 607, respectively, of FIG. 6, acquire and provide relative surface potentials at each shown location of Leg 601 as input to Signal Conditioner 701. Signal Conditioner 701 performs necessary modifications, such as attenuation, filtering, limiting, compensation, and/or conversion upon one or more input signal shown, and may perform more advanced functions, such as integration or differentiation. Conditioned Signals 711, consisting of conditioned version of all input signals described above, is provided by Conditioner 701 as input to Processor 704.

Processor 704, through algorithms known to the art, transforms conditioned accelerometer X, Y, and Z inputs from Conditioned Signals 711 into a standardized reference coordinate system, such as Euler angles, rotation matrices, or quaternions. Leveraging the constant mass of skeletal members concerned, in conjunction with definitions of internalized physiology of the knee of Leg 601 of FIG. 6, Processor 704 as well calculates both vectored gravitic and inertial forces imposed on the joint being treated from conditioned accelerometer inputs. In the example shown in FIG. 6, Processor 704 may calculate axial force magnitudes imposed upon both the medial and lateral condyles of the knee of Leg 701.

At appropriate times, such as at initial use of an embodiment of the invention or upon recognition of previously unseen movement or force conditions, Processor 704 determines and stores the mathematical relationship between joint movement and/or force, such as calculated axial condylar forces of the knee, and conditioned potentials measured at any one or more of Electrodes 705. 706, and 707. In that the time constants of fluid flow within the joint, and hence the streaming potentials so generated, may be much longer than those of the causal forces, temporal aspects of this determined relationship or alternately of any or all elements of Conditioned Signals 711 may be calculated as well.

Calculated relationships between joint movement and/or force and measured electrode potentials are stored, preferably as coefficients, in Processor 704 memory. Read/write access to these stored relationships is provided through External Input/Output Interface 713, optionally with different access restrictions between user and provider access. These relationships may therefore be read for joint diagnostic purposes, modified, or written directly by the user and/or provider, through External Interface 713.

For each relationship between incident forces and streaming potentials so calculated and stored, Controller 604 may be, through modification via External Interface 713, in possession of a desirous modification to be performed upon the calculated relationship. Input of desired relationship modifications to Controller 604 may be through any means known to the art, such as wired, wireless, infrared, etc. Examples of desired modification input may be direct input through an external computer by a health practitioner, notification of painful activity by the patient through wireless means, or detection by contemporaneous Controller software of unbalanced streaming potentials within the joint. Combined input forms of desired modifications, such as use of a practitioner-supplied scalar in conjunction with patient-identified pain, are anticipated.

In subsequent normal operation, Processor 704, in response to predetermined, user-specified, and/or heuristically-determined conditions of one or more constituents of Conditioned Signal 711, determines and controls stimulation current to be applied at one or more electrode locations through output of Medial and Lateral Stimulation Commands 709 and 710, which correspond to Stimulation Commands 609 and 610 of FIG. 6, which are provided as input to Stimulator 712. At least one characteristic, such as intensity, of each element of Stimulation Commands 709 and 710 is calculated directly from at least one said stored relationship, as excited by one or more of joint movement and/or force. In other words, in an embodiment each stimulation output is a known function of a joint movement and/or force.

Stimulator 712, under control of Command 709 and/or 710, delivers dynamic individually-controlled stimulation currents to one or more of Electrodes 706, 707, and/or 708. Stimulation outputs may be of any topology capable of sinking and/or sourcing controlled current and/or voltage, although bilateral controlled current is preferred. To facilitate optional measurement of skin surface potentials, ability to control output impedance of Stimulator 712 outputs is advantageous. Currents applied by Stimulator 712 to Electrodes 706, 707, and/or 708 then stimulate underlying tissue of Leg 601 of FIG. 6 in a localized fashion.

Following the FIG. 6 example, an embodiment may calculate medial condylar axial force within the knee of Leg 601 of FIG. 6 from Accelerometer 702 and 703 inputs, measure concurrent differential voltage between Electrodes 706 and 7707, calculate and store the average dynamic causal relationship between the two, allow provider modification of this stored causal relationship, and subsequently provide stimulation current between Electrodes 706 and 707 which follow this modified causal relationship, as controlled by dynamic calculated medial condylar axial force within the knee of Leg 601 of FIG. 6.

Causal relationship modifications may be in any form, such as a simple multiplier, gain and span, or quadratic form; and may originate from any source, such as a medical practitioner, the patient wearing the device, or even additional software executed by an element of Controller 604.

Figure 8:
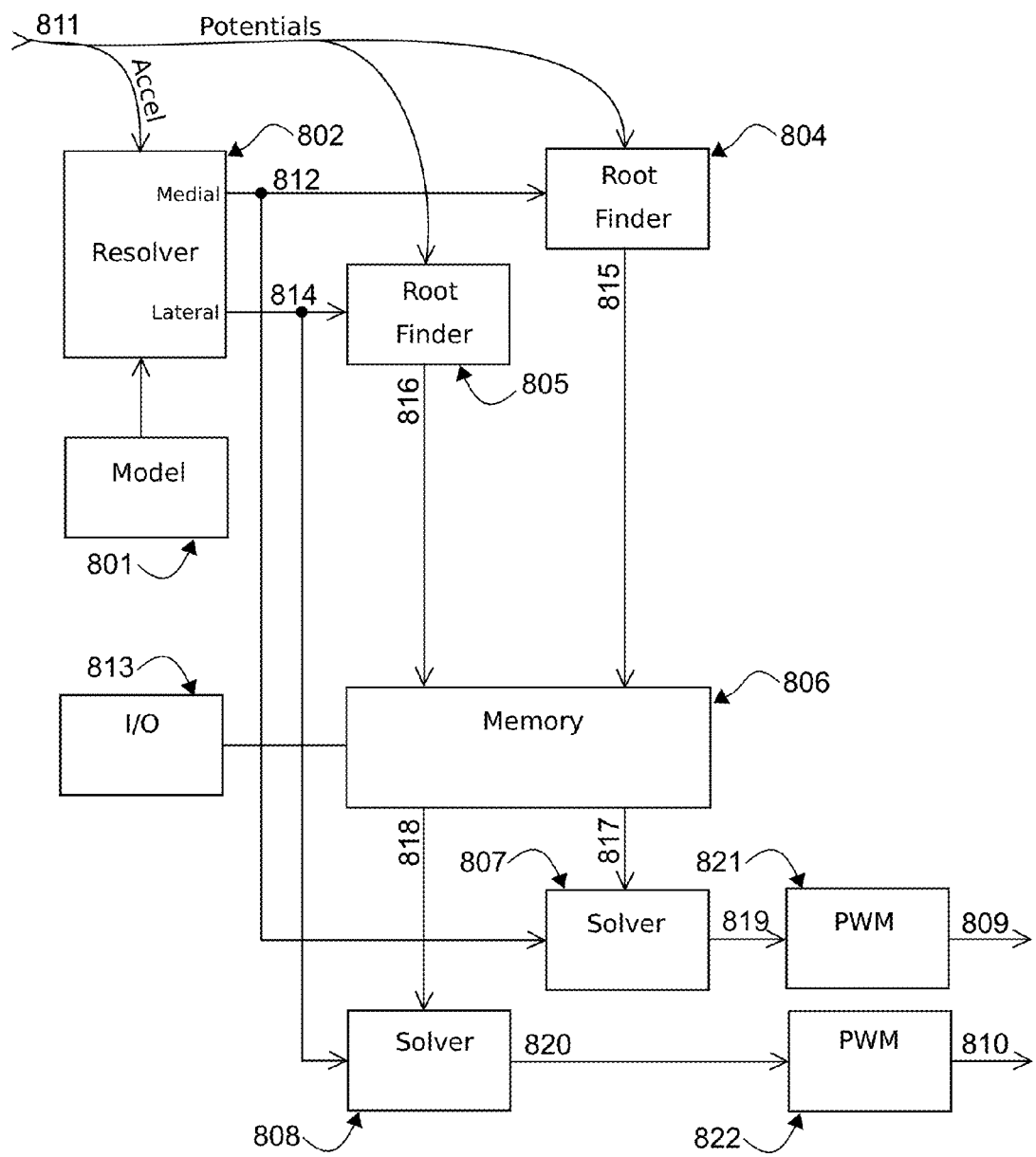
FIG. 8 shows architectural details of the processing element of an embodiment of the invention.

Referring now to FIG. 8 Medial and Lateral Stimulation Commands 809 and 810 correspond respectively to both Commands 609 and 610 of FIG. 6 and Commands 709 and 710 of FIG. 7; Conditioned Signals 811 corresponds to Signals 711 of FIG. 277; and External Input/Output Interface 813 corresponds to External Interface 713 of FIG. 7.

Model 801 provides structural definitions and constants of the appropriate joint to Model Resolver 802, which, under excitement of Conditioned acceleration inputs ultimately from Accelerometers 602 and 603 of FIG. 6, provides dynamic Medial Axial Force 812 and Lateral Axial Force 814 as outputs. Medial Force 812 is supplied as input to both Root Finder 804 and Polynomial Solver 807; Lateral Force 814 is supplied as input to\ both Root Finder 805 and Polynomial Solver 808.

Root Finders 804 and 805 as well receive as inputs conditioned electrode potential presumably ultimately from Electrodes 606 (Medial) and 608 (Lateral) of FIG. 6. From said force and potential inputs, Root Finder 804 provides as output dynamic Calculated Relationship 815 between modeled axial force incident upon the medial condyle of the joint and resultant potential imposed by dynamic elements within the knee at Electrode 606 of FIG. 6. Similarly, Root Finder 805 provides as output dynamic Calculated Relationship 816 between modeled axial force incident upon the lateral condyle of the joint and resultant potential imposed by dynamic elements within the knee at Electrode 608 of FIG. 6. Specific algorithms used within Root Finders 804 and 805 may vary from simple division to more complex iterative methods such as Brent's Method, depending upon the order of the overall system, as is known in the art. Relationship Outputs 815 and 816 of Root Finders 804 and 805, respectively, are presumably in coefficient form, appropriate to the order, but may be expressed in any form known to the art, such as coefficients of gain/span (Ax +B) or quadratic form.

Note that temporal aspects are optionally included in Calculated Relationships 815 and 816, which may therefore include determined time constant and optionally filter order between application of axial force on a knee condyle and resultant voltage subsequently measured at one or more electrodes. Temporal aspects of his relationship may be expressed and stored in any form known and practiced in the art, such as FIR or IIR coefficients.

At appropriate points in time, such as while a user performs a painful action or upon demand of a health practitioner, Relationships 815 and/or 816 are stored in Memory 806 for subsequent use.

Due to the myriad action and force combinations possible in any human joint, it is assumed that multiple Relationships may be stored in Memory 806, to be accessed appropriately to the current activity of the wearer, as is commonly practiced in the art.

Relationships so stored in Memory 806 may be viewed or displayed by external devices through External Interface 813, which may be implemented through any physical medium in use, such as wired, wireless, infrared, etc. External acquisition of said relationships is intended for diagnostic use by the user or health practitioner. For example, External Interface 813 may consist of a wireless physical layer, accessible by a wireless hand-held device on which Relationships from Memory 806 may be viewed and/or edited. In another embodiment, External Interface 813 may consist of an internet-compatible physical layer with a web page server, such as apache2; facilitating data visibility and editing capability through any web browser. Although not required for all embodiments, there is encryption of otherwise insecure data exchange with other embodiments of the present invention.

Calculated Relationships stored in Memory 806 may as well be changed or directly written through External Interface 813, and/or by additional software executing within Processor 704 of FIG. 7. Any edited Relationship thus stored in Memory 806 therefore represents a Desired Relationship, to be used for control purposes described below.

Medial Force 812 and Lateral Force 814 are as well supplied as inputs to Solver 807 and 808, respectively. Solver 807 also receives as input Desired Relationship 817 from Memory 806, which may be an unaltered or altered version of Calculated Relationship 815 from Root Finder 804. Similarly, Solver 808 also receives as input Desired Relationship 818 from Memory 806, which may be an unaltered or altered version of Calculated Relationship 816 from Root Finder 805.

Under dynamic excitation of Medial Force 812 as described, Solver 807 outputs Desired Potential 819 to Pulse Width Modulator 821, which resultantly provides Medial Stimulation Command 809 to Stimulator 605 of FIG. 6. Stimulator 605 then provides modulated stimulation current to Electrode 606 of FIG. 6, as described above. Similarly, Solver 808, under dynamic excitation of Lateral Force 814, outputs Desired Potential 820 to Pulse Width Modulator 822, which resultantly provides Lateral Stimulation Command 810 to Stimulator 605 of FIG. 6. Stimulator 605 then provides modulated stimulation current to Electrode 608 of FIG. 6, as described above. Although shown as pulse width modulators, Modulators 821 and 822 may use any modulation form, such as pulse density, pulse position, frequency, or even amplitude.

Although voltage and current are used interchangeably above for simplicity, physiology is known to present complex impedances. It is assumed that compensatory measures are to be taken within Processor 704, presumably through analog circuitry or executable software to normalize measured potentials with imposed currents.

Thus, in various embodiments it can be seen that streaming potentials biologically created within Leg 601 of FIG. 6, as transcutaneously measured, may be subsequently modulated by Stimulator 105 of FIG. 1, as the wearer of the embodiment of the invention proceeds through normal activities.

Figure 9:
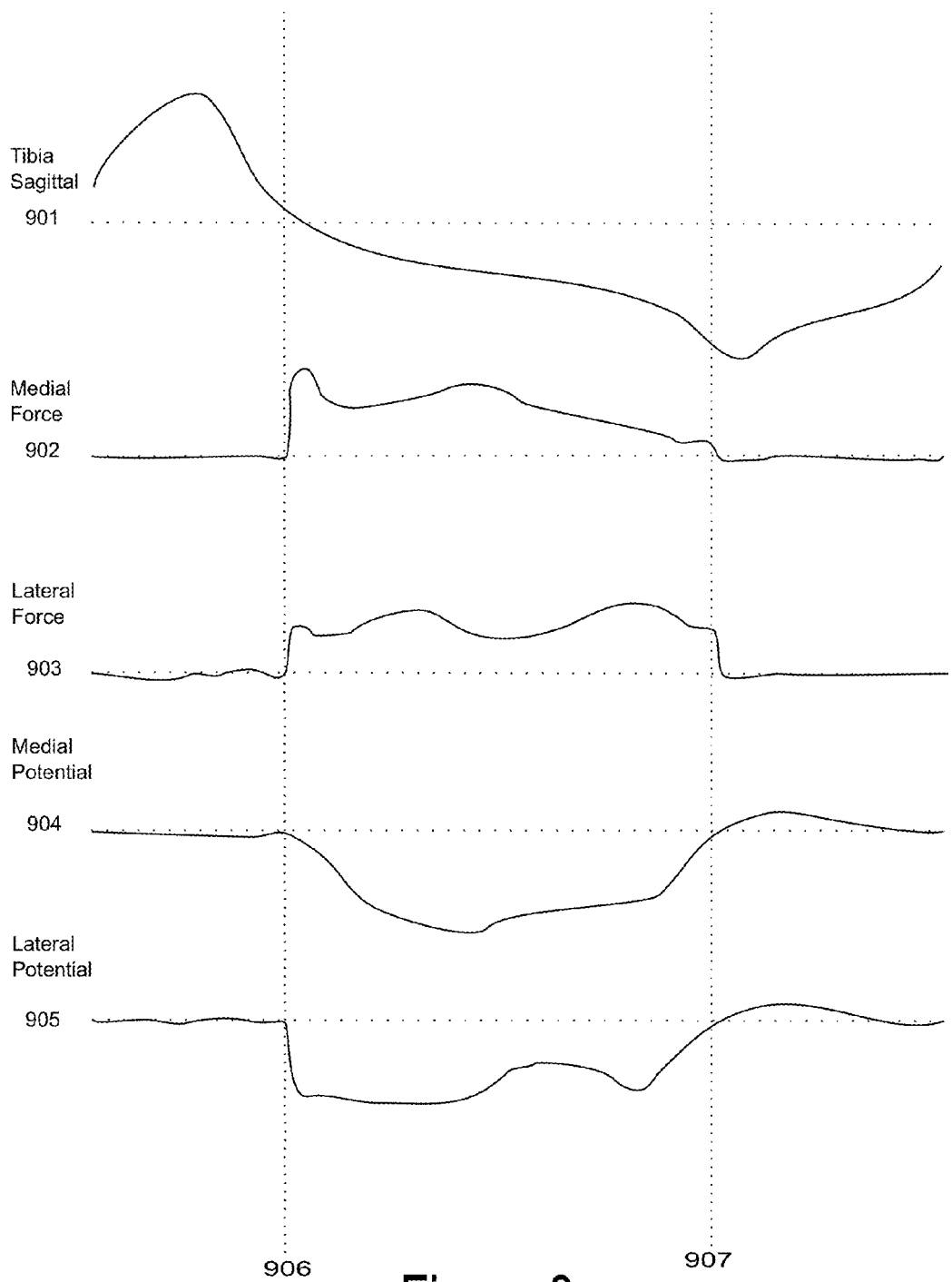
FIG. 9 shows sagittal position, incident forces, and differential voltages naturally imposed by biological streaming potentials on electrodes of the embodiment of FIG. 6 as a wearer of an embodiment of the invention walks normally on a normal level surface.

Referring now to FIG. 9, Trace 901 shows tibial Sagittal Position of Leg 601 of FIG. 6 through stance phase of a gait cycle, with value directly proportional to anterior position. Traces 902 and 903 show axial Medial and Lateral Condylar Forces, respectively. Traces 904 and 905 indicate Streaming Potentials imposed on the medial and lateral sides of the knee, as presented to Electrodes 606 and 608, respectively, relative to Electrode 607, all of FIG. 6. The X axis of FIG. 9 indicates linear time.

At Time Marker 906, heel strike occurs, indicating initial loading. Resultantly, both medial and lateral condylar force immediately increase, as seen in Traces 902 and 903, respectively. As the leg progresses through stance phase, however, oscillation between medial and lateral forces can be seen in Traces 903 and 904, typical of knee instability caused by excessive laxity. Although negative-going streaming potentials can be seen in both Traces 904 and 905 as stance phase is entered after Marker 906, Medial Potential 904 is seen to deviate less and more slowly than Lateral Potential 905, in spite of the fact that Medial Force 902 exceeds Lateral Force 903 at this point by a visible margin.

At Time Marker 907, the foot is no longer weight bearing, as indicated by force cessation in both Medial Force 902 and Lateral Force 903. After Marker 907, Medial Potential 904 and Lateral Potential 905 both move slowly in a positive direction, indicating reversal of fluid flows induced by axial force while loaded.

Attenuation and slow response of streaming potentials is repeatedly seen in joints with compromised cartilage. Potentials shown in Trace 904 between Markers 906 and 907 for the indicated force of Trace 902 therefore could indicate that Leg 601 of FIG. 6 has an eroded medial condyle. In that streaming potentials are induced by flow of fluids containing charged particles, loaded fluid flow through the medial cartilage of Leg 601 of FIG. 6 is therefore presumed to be deficient.

Figure 10:
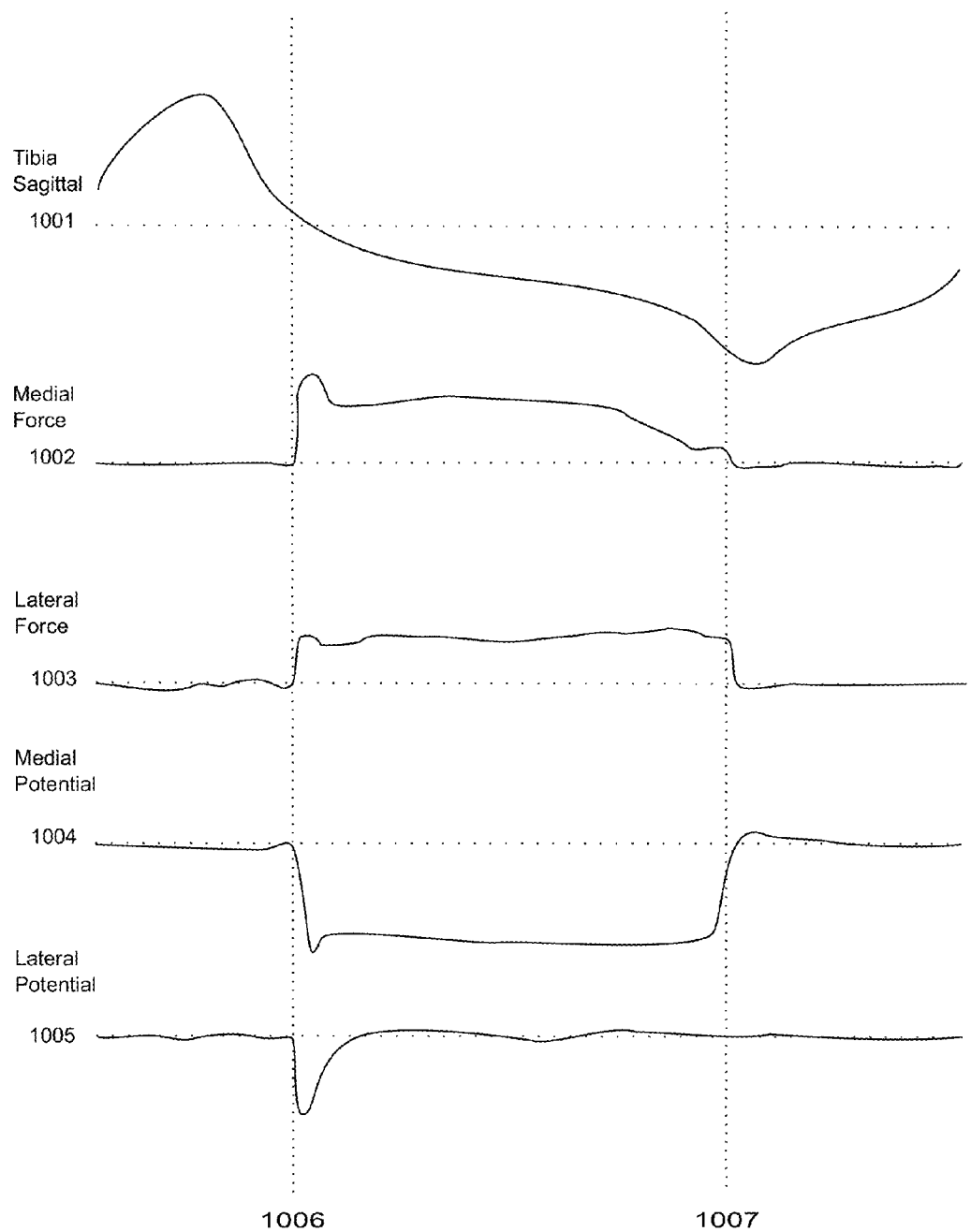
FIG. 10 shows sagittal positions, incident forces, and differential output currents of the embodiment of FIG. 6 as the wearer of the embodiment of the invention walks normally on a level surface.

Referring now to FIG. 10, Trace 1001 shows tibial Sagittal Position of Leg 601 of FIG. 6 through stance phase of a gait cycle, with value directly proportional to anterior position. Traces 1002 and 1003 show axial Medial and Lateral Condylar Forces, respectively. Traces 1004 and 1005 indicate Stimulation Currents to be imposed by the an embodiment of the invention on the medial and lateral sides of the knee, as presented to Electrodes 606 and 608, respectively, relative to Electrode 607, all of FIG. 6. The X axis of FIG. 10 indicates linear time.

(FIGS. 9 and 10 include horizontal dotted lines that are sagittal plumb vertical in 901/1001, and zero in the other traces. Further, traces 904/905 are potentials at the electrodes (without stimulation) that are measured (input connections to 604, which become 811). 1004/1005 are the composite potentials resultant of the body doing what is shown in FIG. 9, and the stimulation. FIG. 10 depicts applying a current, to the electrodes, which modifies the potentials already on those electrodes, making traces 1004 and 1005.)

At Time Marker 1006, sharp increases can again be seen in Medial Force 1002 and Lateral Force 1003, at initial loading. Note, however, that the initial forces indicated in Traces 1002 and 1003 result in immediate negative currents applied to both Electrodes 606 and 608 of FIG. 6, shown in Trace 1004 and 1005, respectively. Current applied to Electrode 606 of FIG. 6 can be seen in Trace 1004 to decrease non-linearly with decreasing force in Trace 1002 until Time Marker 1007, at which point current returns to zero. Current applied to Electrode 608 of FIG. 6 can be seen in Trace 1005 to quickly decrease non-linearly in opposing fashion to Trace 1004, attaining zero current before Time Marker 1007.

Note that the force oscillation between Medial Force 1002 and Lateral Force 1003 between Markers 1006 and 1007 is diminished from that shown in FIG. 9. Stability has in this example been improved by simultaneous stimulation current to both medial and lateral sides of the knee upon loading at Time Marker 1006.

Stimulation Current 1004 shows continuous current application to medial Electrode 606 of FIG. 6, non-linearly proportional to Medial Force 1002, until force cessation at Marker 1007. The purpose of this current is to encourage fluid flow through the medial cartilage, in spite of mechanical damage to the joint. The rapid Stimulation Current 1005 diminution shown during Lateral Force 1003 loading can be seen to cease modulation of natural streaming potentials after the initial stabilization current at Marker 1006.

Time constants, polynomial and filter orders, modulation forms, and streaming potential modulation strategies are all anticipated to be varied widely without departing the scope of embodiments of the invention as described herein.

By the preceding disclosure, individualized streaming potentials in and/or around a compromised joint or body part can be seen to be modulated in a therapeutic fashion by embodiments of the present invention. Through direct adaptation to the individual user, use of embodiments of the invention need not be constrained to clinical settings. It can furthermore be seen that potentials in and around the joint may be dynamically modulated.

Although shown in conjunction with electrical stimulation, alternate stimulation means, such as magnetic stimulation, are anticipated. Embodiments of the invention can be seen to be amenable to any control means known to the art, such as analog and/or digital electronic, pneumatic, or hydraulic control.

While the present invention has been described with respect to a limited number of embodiments, those skilled in the art will appreciate numerous modifications and variations therefrom. It is intended that the appended claims cover all such modifications and variations as fall within the true spirit and scope of this present invention.

What is claimed is:

1. An apparatus comprising:
   at least one memory;
   at least one controller, coupled to the memory, programmed to perform operations comprising:
   sensing a first physical orientation between a patient's first and second appendage portions, which couple together via a joint, during a baseline state;
   sensing a second physical orientation between the first and second appendage portions during a non-baseline state;
   determining an orientation differential between the first and second physical orientations;
   determining a current stimulation characteristic, corresponding to first current, based on the orientation differential; and
   stimulating at least one of the joint, first appendage portion, and second appendage portion with the first current in a hysteretic closed loop relationship relating the current stimulation characteristic to the orientation differential wherein the stimulating with the first current in the closed loop relationship includes adjusting the current stimulation characteristic in proportion to the orientation differential.

2. The apparatus of claim 1, wherein the current stimulation characteristic comprises at least one of pulse width duration, amplitude, and polarity.

3. The apparatus of claim 1, wherein determining the orientation differential comprises determining a differential between (a) a first coronal plane angle between the patient's femur and tibia in the first physical orientation, and (b) a second coronal plane angle between the patient's femur and tibia in the second physical orientation.

4. The apparatus of claim 3 wherein the baseline state includes a non-loaded state where the patient is not standing on the femur and tibia and the non-baseline state includes a loaded state where the patient is standing on the femur and tibia.

5. The apparatus of claim 1, the operations comprising:
   determining a second current stimulation characteristic, corresponding to second current, based on the orientation differential; and
   stimulating at least another of the joint, first appendage portion, and second appendage portion with the second current in another closed loop relationship relating the second current stimulation characteristic to the orientation differential.

6. The apparatus of claim 5, the operations comprising stimulating with the first and second current via a mode comprising at least one of (a) simultaneously stimulating with the first and second current, and (b) multiplexed stimulation with the first and second current.

7. The apparatus of claim 6, the operations comprising:
   stimulating with the first current between a first electrode, configured to be located lateral to the patient's joint and below the first appendage portion, and a second electrode configured to be located on the first appendage portion; and
   stimulating with the second current between a third electrode, configured to be located medial to the patient's joint and below the first appendage portion, and the second electrode.

8. The apparatus of claim 5 wherein the first current is unequal to the second current.

9. The apparatus of claim 5 wherein the first current has a first pulse width duration unequal to a second pulse width duration for the second current.

10. The apparatus of claim 1, the operations comprising:
    sensing a first transcutaneous potential for the joint and a first force on the joint;
    determining a first relationship between the first transcutaneous potential and the first force;
    sensing a second transcutaneous potential for the joint and a second force on the joint;
    determining a second relationship between the second transcutaneous potential and the second force;
    determining a relationship differential between the first and second relationships;
    determining another current stimulation characteristic, corresponding to second current, based on the relationship differential; and
    stimulating at least one of the joint, the first appendage portion, and the second appendage portion with the second current in another closed loop relationship relating the another current stimulation characteristic to the relationship differential.

11. The apparatus of claim 10 wherein the first and second transcutaneous potentials include first and second streaming potentials.

12. An apparatus comprising:
    at least one memory;
    at least one controller, coupled to the memory, programmed to perform operations comprising:
    sensing a first physical orientation between a patient's first and second appendage portions, which couple together via a joint, during a baseline state;
    sensing a second physical orientation between the first and second appendage portions during a non-baseline state;
    determining an orientation differential between the first and second physical orientations;
    determining a current stimulation characteristic, corresponding to first current, based on the orientation differential;
    stimulating at least one of the joint, first appendage portion, and second appendage portion with the first current in a closed loop relationship relating the current stimulation characteristic to the orientation differential;
    determining a second current stimulation characteristic, corresponding to second current, based on the orientation differential;

stimulating at least another of the joint, first appendage portion, and second appendage portion with the second current in another closed loop relationship relating the second current stimulation characteristic to the orientation differential;
stimulating with the first and second current via a mode comprising at least one of (a) simultaneously stimulating with the first and second current, and (b) multiplexed stimulation with the first and second current;
stimulating with the first current between a first electrode, configured to be located lateral to the patient's joint and below the first appendage portion, and a second electrode configured to be located on the first appendage portion; and
stimulating with the second current between a third electrode, configured to be located medial to the patient's joint and below the first appendage portion, and the second electrode.

13. The apparatus of claim 12 wherein the first current is unequal to the second current.

14. The apparatus of claim 12 wherein the first current has a first pulse width duration unequal to a second pulse width duration for the second current.

15. An apparatus comprising:
at least one memory;
at least one controller, coupled to the memory, programmed to perform operations comprising:
sensing a first physical orientation between a patient's first and second appendage portions, which couple together via a joint, during a baseline state;
sensing a second physical orientation between the first and second appendage portions during a non-baseline state;
determining an orientation differential between the first and second physical orientations;
determining a current stimulation characteristic, corresponding to first current, based on the orientation differential;
stimulating at least one of the joint, first appendage portion, and second appendage portion with the first current in a closed loop relationship relating the current stimulation characteristic to the orientation differential;
sensing a first transcutaneous potential for the joint and a first force on the joint;
determining a first relationship between the first transcutaneous potential and the first force;
sensing a second transcutaneous potential for the joint and a second force on the joint;
determining a second relationship between the second transcutaneous potential and the second force;
determining a relationship differential between the first and second relationships;
determining another current stimulation characteristic, corresponding to second current, based on the relationship differential; and
stimulating at least one of the joint, the first appendage portion, and the second appendage portion with the second current in another closed loop relationship relating the another current stimulation characteristic to the relationship differential.

16. The apparatus of claim 15 wherein the first and second transcutaneous potentials include first and second streaming potentials.

* * * * *